US 9,475,632 B2

(12) United States Patent
Toma et al.

(10) Patent No.: US 9,475,632 B2
(45) Date of Patent: Oct. 25, 2016

(54) SYRINGE-TYPE SQUIRT CONTAINER

(71) Applicants: Toru Toma, Tokyo (JP); Shigeo Iizuka, Tokyo (JP)

(72) Inventors: Toru Toma, Tokyo (JP); Shigeo Iizuka, Tokyo (JP)

(73) Assignee: YOSHINO KOGYOSHO CO., LTD., Tokyo (JP)

( * ) Notice: Subject to any disclaimer, the term of this patent is extended or adjusted under 35 U.S.C. 154(b) by 0 days.

(21) Appl. No.: 14/652,495

(22) PCT Filed: Nov. 14, 2013

(86) PCT No.: PCT/JP2013/006700
§ 371 (c)(1),
(2) Date: Jun. 16, 2015

(87) PCT Pub. No.: WO2014/103139
PCT Pub. Date: Jul. 3, 2014

(65) Prior Publication Data
US 2015/0329271 A1    Nov. 19, 2015

(30) Foreign Application Priority Data

Dec. 27, 2012  (JP) ................................. 2012-286325
Sep. 30, 2013  (JP) ................................. 2013-205109

(51) Int. Cl.
*B05B 1/26* (2006.01)
*B05B 1/34* (2006.01)
*B65D 83/00* (2006.01)
*A61M 3/02* (2006.01)
*A61M 5/30* (2006.01)
*B05B 11/02* (2006.01)
*A61M 31/00* (2006.01)
*A61M 11/00* (2006.01)

(52) U.S. Cl.
CPC ........ *B65D 83/0033* (2013.01); *A61M 3/0279* (2013.01); *A61M 5/30* (2013.01); *A61M 5/3007* (2013.01); *A61M 31/00* (2013.01); *B05B 1/3447* (2013.01); *B05B 11/02* (2013.01); *A61M 11/007* (2014.02)

(58) Field of Classification Search
CPC ....... B05B 7/10; B05B 1/3442; B05B 1/341; B05B 9/0403; B05B 1/34; B05B 1/3415
USPC ................................ 239/461, 463, 482, 483
See application file for complete search history.

(56) References Cited

U.S. PATENT DOCUMENTS

2002/0017294 A1   2/2002  Py
2003/0111552 A1   6/2003  Vedrine et al.
(Continued)

FOREIGN PATENT DOCUMENTS

EP    1 092 447 A2    4/2001
JP    2001-137344 A   5/2001
(Continued)

OTHER PUBLICATIONS

Feb. 10, 2014 International Search Report issued in International Patent Application No. PCT/JP2013/006700.
May 24, 2016 Search Report issued in European Patent Application No. 13868039.2.

*Primary Examiner* — Davis Hwu
(74) *Attorney, Agent, or Firm* — Oliff PLC

(57) ABSTRACT

Provided is a syringe-type ejecting container that is capable of ejecting even a small amount of a content medium. Such an ejecting container includes an ejecting unit and an operation unit. The operation unit includes a syringe having a front end tubular portion, a rod extending through an inside of the front end tubular portion, and an operation shaft that causes the rod to project from the front end tubular portion. The ejecting unit includes a pipe that is mounted to the front end tubular portion and that is filled with a content medium, a plunger that is arranged inside the pipe, a nozzle that is mounted over an outside of a front end of the pipe, and a spin element that is arranged inside the nozzle close to the ejection hole and that is formed with a swirling groove leading to the ejection hole.

10 Claims, 10 Drawing Sheets

(56) References Cited

U.S. PATENT DOCUMENTS

2010/0095957 A1 4/2010 Corbacho
2010/0114158 A1* 5/2010 Hattan ............. A61B 17/00491
                                                                606/214
2012/0253272 A1* 10/2012 Menassa ................ A61M 5/30
                                                                604/68

FOREIGN PATENT DOCUMENTS

| JP | 2004-535845 A | 12/2004 |
| JP | 2011-078801 A | 4/2011 |
| WO | 95/00195 A1 | 1/1995 |
| WO | 02/055133 A2 | 7/2002 |
| WO | 2013/080558 A1 | 6/2013 |

* cited by examiner

X-X section

Y-Y section

Z-Z section

SYRINGE-TYPE SQUIRT CONTAINER

TECHNICAL FIELD

This disclosure relates to a syringe-type squirt (ejecting) container that is capable of pushing an operation shaft into a syringe to eject a content medium to the outside.

BACKGROUND

Examples of conventionally known syringe-type ejecting containers include the one including a spray nozzle embedded with a valve. The spray nozzle is mounted to a syringe (barrel) filled with the content medium, and the content medium is pushed out and sprayed by a piston (Refer to Patent Literature 1, for example).

CITATION LIST

Patent Literature

PTL 1: JP2001-137344A

SUMMARY

However, such a conventional syringe-type ejecting container fills the content medium in the operation device operated by a user, and therefore, even because a small amount of the content medium is desired to be sprayed, downsizing of the syringe adversely affects usability. Accordingly, the conventional syringe-type ejecting container is unsuitable for spraying a small amount of the content medium.

It would be helpful to provide a novel syringe-type ejecting container that is capable of ejecting even a small amount of the content medium.

One aspect of this disclosure resides in a syringe-type ejecting container, including: an operation unit operated by a user; and an ejecting unit through which a content medium is ejected.

The operation unit includes a syringe having a front end tubular portion, a rod extending through an inside of the front end tubular portion, and an operation shaft that causes the rod to project from the front end tubular portion.

The ejecting unit includes a pipe member that is mounted to the front end tubular portion and that is filled with the content medium, a plunger that is arranged inside the pipe member to push out the content medium, a nozzle that is mounted over an outside of a front end of the pipe member and that is provided with an ejection hole, and a spin element that is arranged inside the nozzle close to the ejection hole and that is formed with a swirling groove configured to circulate the content medium to the ejection hole.

The spin element may include a main body portion that is arranged between the nozzle and the pipe member and an insertion portion that is inserted into the pipe member.

Preferably, the insertion portion includes a locking portion that is locked to an inner side of the pipe member.

The insertion portion may include at least one cut-out portion.

In the syringe-type ejecting container according to the above aspect, the ejecting unit may be detachably mounted to the operation unit.

In the syringe-type ejecting container according to this disclosure, the operation shaft included in the operation unit is pushed to cause the rod to project from the front end tubular portion of the syringe. Subsequently, the rod projecting from the front end tubular portion, together with the plunger embedded in the pipe member included in the ejecting unit, pushes the content medium toward the spin element. The content medium passes the swirling groove formed in the spin element to spin before pushing out to the ejection hole provided in the nozzle.

In this way, the ejecting container according to this disclosure sends the content medium filled in the ejecting unit out to the ejection hole while applying spinning force to the content medium, thereby ejecting the content medium.

Furthermore, the ejecting container according to this disclosure fills the content medium in the ejecting unit, and therefore, the operation unit for ejecting the content medium may be configured separately. As a result, only the ejecting unit filled with the content medium may be downsized without downsizing the operation unit. Accordingly, the ejecting container according to this disclosure is particularly effective when only a small amount of the content medium is desired to be sprayed without the need for compromising the operability.

DETAILED DESCRIPTION

The following describes various embodiments of a syringe-type ejecting container of this disclosure in detail with reference to the drawings. In the description below, the term front-rear direction is used to refer to the direction in which the syringe-type ejecting container is pushed (the direction in which the content medium is ejected) as the front direction and is also used to refer to the opposite direction (the direction that is opposite to the direction of the pushing force applied to the syringe-type ejecting container) as the rear direction.

Figure 1:
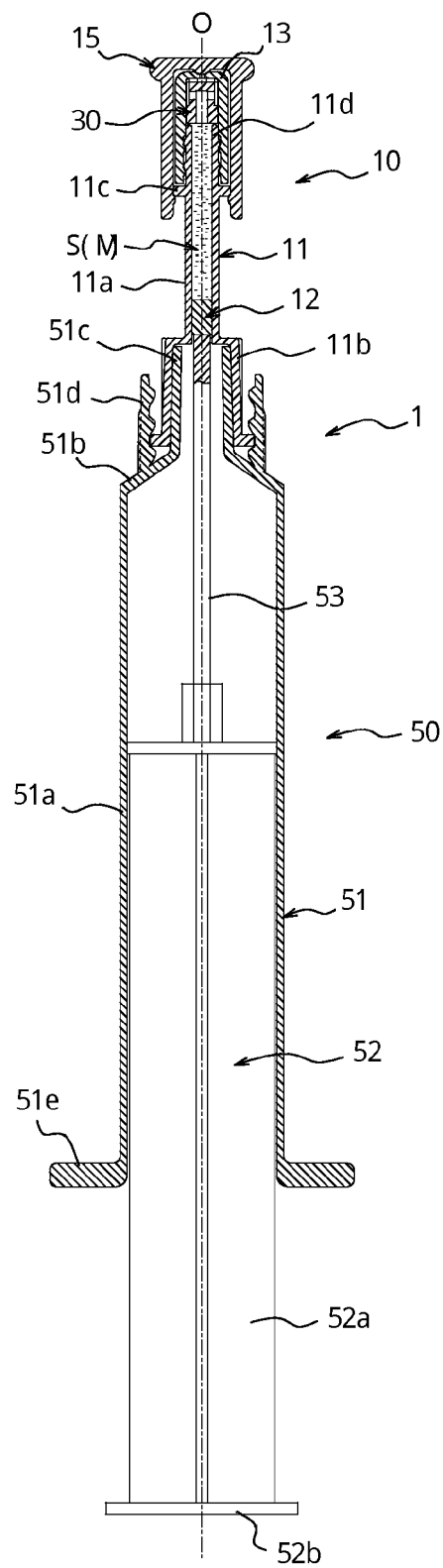
FIG. 1 is a sectional view of a part of a syringe-type ejecting container according to the first embodiment.

In FIG. 1, reference numeral 1 denotes a syringe-type ejecting container (hereinafter, called "ejecting container") according to the first embodiment. The ejecting container 1 includes an operation unit 50 operated by a user and an ejecting unit 10 through which a content medium M is ejected.

To start with, the operation unit 50 includes a syringe 51. The syringe 51 includes, on a front side thereof, an annular shoulder portion 51b formed on one end of a hollow trunk portion 51a. The syringe 51 also includes a front end tubular portion 51c that is integrally formed via the shoulder portion 51b and that has a smaller diameter than the trunk portion 51a. The front end tubular portion 51c is provided inside thereof with an inner passage that is in communication with space formed inside the trunk portion 51a. The syringe 51 also includes a fitting tubular portion 51d surrounding the front end tubular portion 51c. Furthermore, the syringe 51 includes, on a rear side thereof, a finger rest 51e.

The operation unit 50 also includes an operation shaft 52. The operation shaft 52 includes a main body 52a, which is slidably accommodated within the syringe 51, and a pressed portion 52b, which is arranged on the rear of the main body 52a and which receives pushing force from the user. The main body 52a is provided on a front end thereof with a plunger rod (a rod) 53. The plunger rod 53 has a tip (a front end) portion that is arranged inside the front end tubular portion 51c of the syringe 51. With the above structures, when the user pushes the operation shaft 52 while resting the fingers on the finger rest 51e of the syringe 51, the plunger rod 53 is projected from the front end tubular portion 51c of the syringe 51. According to the present embodiment, the plunger rod 53 may be an integral or a separate part of the operation shaft 52.

The operation unit 50 is configured as an operation device as described above, whereas the ejecting unit 10 serves as an ejecting nozzle.

Figure 2A:
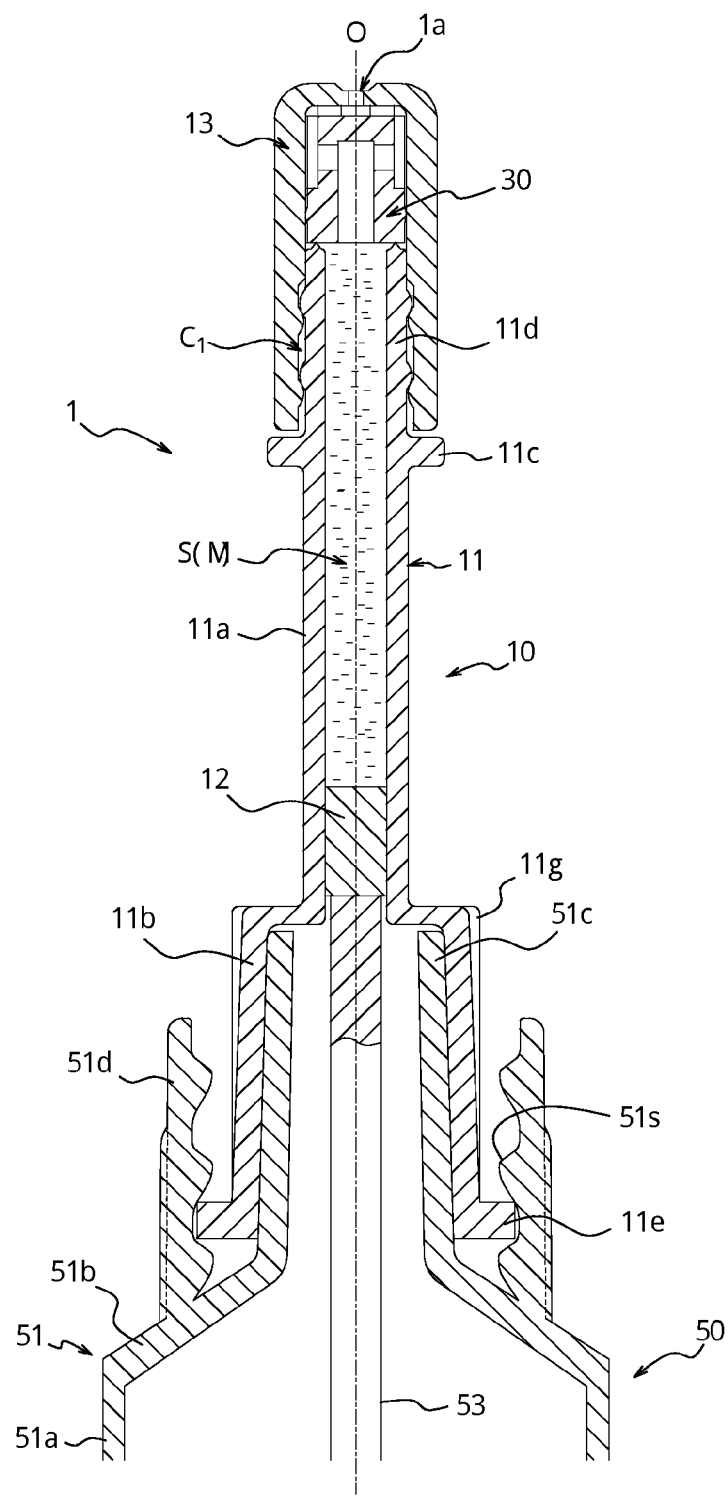
FIG. 2A is an enlarged sectional view of the vicinity of an ejecting unit of the syringe-type ejecting container illustrated in FIG. 1.

As illustrated in FIG. 2A, the ejecting unit 10 includes a pipe member 11 that is mounted to the front end tubular portion 51c of the syringe 51. The pipe member 11 includes a small-diameter portion 11a and a large-diameter portion 11b that has a larger inner diameter than the small-diameter portion 11a. Within the large-diameter portion 11b, the front end tubular portion 51c of the syringe 51 is accommodated. The large-diameter portion 11b is also formed with a rear end portion 11e of the pipe member 11. The rear end portion 11e of the pipe member 11 forms a flange portion that serves as a screw portion, and the flange portion is detachably screwed to a screw portion 51s formed on an inner side of the fitting tubular portion 51d of the syringe 51. This allows the ejecting unit 10 to be screwed to the syringe 51 as illustrated in the figure, and accordingly, mounted to the operation unit 50. The large-diameter portion 11b of the pipe member 11 is provided with a plurality of longitudinal ribs 11g that is located at an interval around a container axis line O and that extends along the container axis line O. The longitudinal ribs 11g serve as anti-slippery ribs during operations of the pipe member 11. According to the present embodiment, as a method of connecting the pipe member 11 with the syringe 51, an existing method such as undercut fitting taking advantage of irregularities may be selected.

Furthermore, on a rear end side of the pipe member 11 (the small-diameter portion 11a), a plunger 12 is arranged. The plunger 12 may be slide on an inner circumferential surface of the pipe member 11 in a liquid-tight manner. Accordingly, the inside of the pipe member 11 (the small-diameter portion 11a) may be filled with the content medium M.

The small-diameter portion 11a of the pipe member 11 is provided with a neck ring 11c extending circumferentially around the container axis line O. The neck ring 11c partitions a front end portion 11d of the pipe member 11 off from a remaining portion. Over the outside of the front end portion 11d, a nozzle 13 is mounted. The nozzle 13 is provided in a tip (a front end) thereof with an ejection hole 1a. Furthermore, the nozzle 13 is fixed to the front end portion 11d of the pipe member 11 by a fixing portion $C_1$. Examples of the fixing portion $C_1$ include an undercut fitting portion taking advantage of irregularities as illustrated in the figure. However, the fixing portion $C_1$ is not limited to the undercut fitting portion and may also use any other fixing method such as screwing utilizing a screw portion. The neck ring 11c serves to prevent the nozzle 13 from falling off from the pipe member 11 by a rear end of the nozzle 13, which projects relative to an outer circumferential surface of the pipe member 11, being caught by an operator's hand or the like.

Figure 2B:
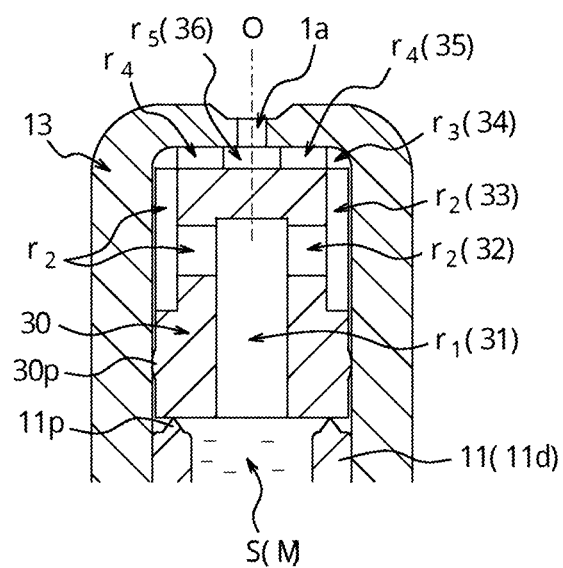
FIG. 2B is an enlarged sectional view of the vicinity of a front end of the ejecting unit illustrated in FIG. 2A.

Inside a front end of the nozzle 13, a spin element 30 is further arranged. The spin element 30 has a columnar shape. The spin element 30 has an outer circumferential surface that is slidable on an inner circumferential surface of the nozzle 13 in a liquid-tight manner. In the present embodiment, preferably as illustrated in FIG. 2B, the outer circumferential surface of the spin element 30 is formed with an annular projection 30p extending circumferentially around the container axis line O. Accordingly, a contacting portion between the inner circumferential surface of the nozzle 13 and the outer circumferential surface of the spin element 30 remains in a more liquid-tight state.

Furthermore, the spin element 30 has one end surface (a front end surface) that may be abutted against an inner surface of the front end of the nozzle 13. Accordingly, a contacting portion between the front end surface of the spin element 30 and the inner surface of the front end of the nozzle 13 remains in a liquid-tight state. On the other hand, the other end (a rear end surface) of the spin element 30 contacts a front end surface (i.e. an end surface of the front end portion 11d) of the pipe member 11. Accordingly, a contacting portion between the rear end surface of the spin element 30 and the front end surface of the pipe member 11 remains in a liquid-tight state. In the present embodiment, preferably the front end surface of the pipe member 11 is formed with an annular projection 11p extending circumferentially around the container axis line O. Accordingly, a contacting portion between the rear end surface of the spin element 30 and the front end surface of the pipe member 11 remains in a more liquid-tight state. Additionally, according to the present embodiment, the method of sealing between the front end surface of the pipe member 11 and the rear end surface of the spin element 30 is not limited to the annular projection 11p. For example, the liquid-tight state may also be maintained by providing an inner ring in the spin element 30 or by providing an O-ring between the pipe member 11 and the spin element 30.

As illustrated in FIG. 2A, inside the pipe member 11, there is formed, along with the spin element 30, filling space S of the content medium M defined by the plunger 12. That is to say, in the present embodiment, the ejecting unit 10 includes the pipe member 11, the plunger 12, the nozzle 13, and the spin element 30.

Figure 4:
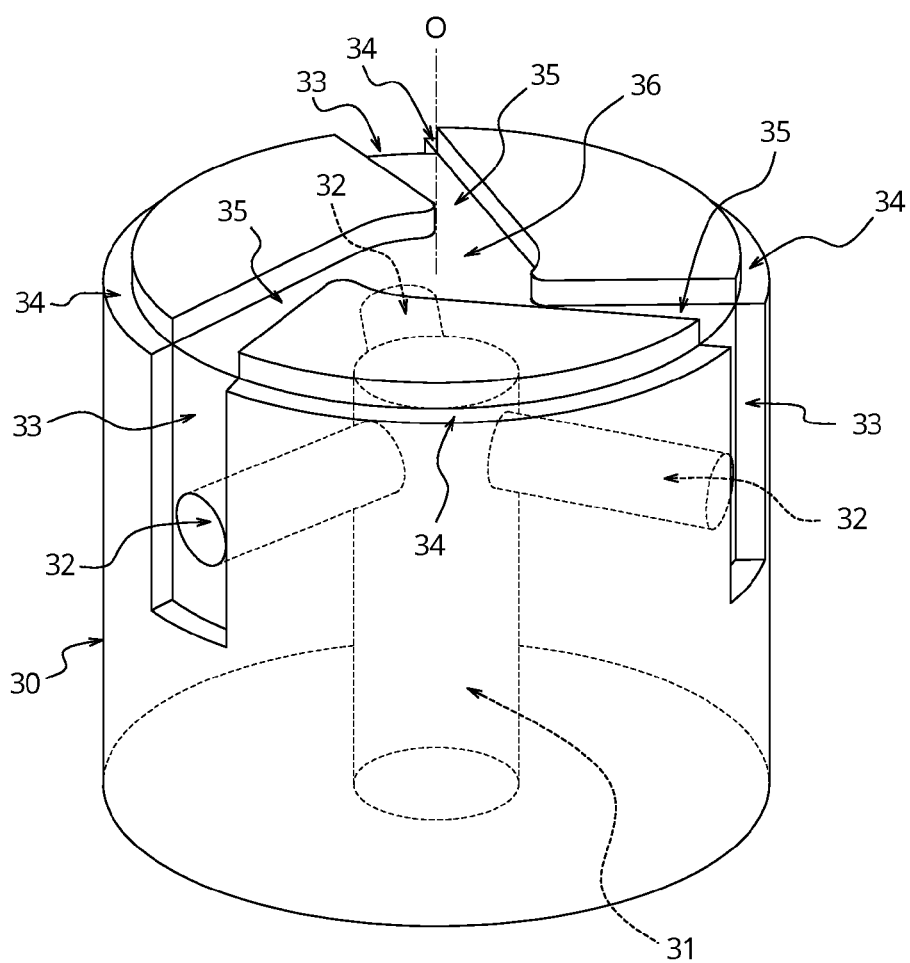
FIG. 4 is a schematic perspective view of a spin element according to FIG. 1.

In the present embodiment, as illustrated in FIG. 2B, the spin element 30 is formed with an inner passage 31. The inner passage 31 opens to the rear end surface of the spin element 30. As illustrated in FIG. 4, the spin element 30 is formed with at least one (three in the present embodiment) through holes 32 extending from the inner passage 31 in the radial direction. The spin element 30 also has a lateral surface formed with grooves 33 in correspondence with the positions of the through holes 32. The grooves 33 each extend along the container axis line O and cut out a portion of the front end surface of the spin element 30. The front end surface of the spin element 30 also has a periphery that is formed with an annular cut-out 34 extending circumferentially around the container axis line O. On the front end surface of the spin element 30, swirling grooves 35 connecting to the grooves 33 are formed. These three swirling grooves 35 each extend from the cut-out 34 toward the container axis line O while swirling around the container axis line O. Thus, the three swirling grooves 35 join in a cylindrical joining groove 36 formed on the front end surface of the spin element 30.

That is to say, in the present embodiment, by incorporating the pipe element 11 and the spin element 30 inside the nozzle 13, as illustrated in FIG. 2B, an introduction flow path $r_1$ (31) that communicates with the filling space S of the content medium M, branched flow paths $r_2$ (32 and 33) that separate the introduction flow path $r_1$ into three flow paths, an annular flow path $r_3$ (34) that connects the three branched flow paths $r_2$ in an annular form, three swirling flow paths $r_4$ (35) that connect to the three branched flow paths $r_2$ via the annular flow path $r_3$ (34), and a joining portion $r_5$ (36) that connects the swirling flow paths $r_4$ to the ejection hole 1a are formed between the pipe member 11 and the nozzle 13. In the present embodiment, preferably as illustrated in FIG. 4, each of the branched flow paths $r_2$ (32 and 33) is aligned with the corresponding one of the swirling flow paths $r_4$ (35) via the annular flow path $r_3$ (34).

Additionally, the branched flow path $r_2$ and the swirling flow path $r_4$ may also be arranged to be offset from each other around the container axis line O, so that the annular flow path $r_3$ (34) serves as a bypass flow path. Furthermore, the number of the branched flow paths $r_2$ does not need to correspond to that of the swirling flow paths $r_4$ and may be at least one.

In the following, a description is given of a method of use of the ejecting container 1 with reference to FIGS. 1 to 3.

As illustrated in FIG. 1, once the user mounts the ejecting unit 10 to the operation unit 50, as illustrated in FIG. 2A, a rear end of the plunger 12 serves as a pressed portion that receives pressing force from the tip (the front end) of the plunger rod 53. By thus being pushed by the plunger rod 53, the plunger 12 pushes the content medium M filled in the filling space S toward the spin element 30. The content medium M pushed toward the spin element 30 is then introduced from the introduction flow path $r_1$ into the spin element 30 as indicated by an arrow outline with a blank inside in FIG. 3. The content medium M introduced into the spin element 30 is then separated into the three branched flow paths $r_2$ to be distributed toward the lateral surface of the spin element 30. The distributed content medium M is fed to the three swirling flow paths $r_4$ located on the front end surface of the spin element 30 through the annular flow path $r_3$. Accordingly, after being pushed toward the spin element 30, the content medium M passes the swirling flow paths $r_4$ formed in the spin element 30 to spin around the container axis line O before joining and swirling in the joining portion $r_5$.

Figure 3:
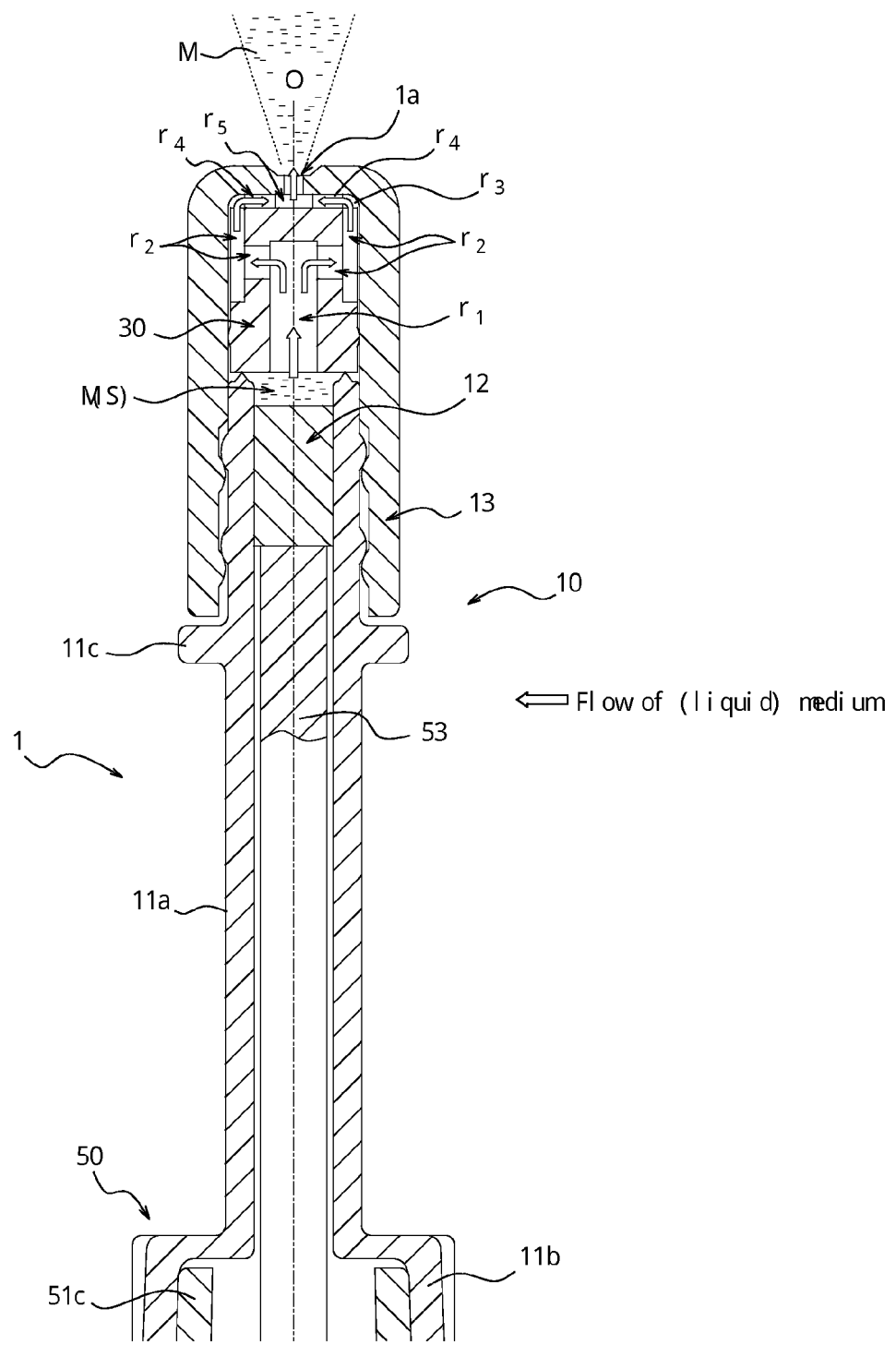
FIG. 3 is an enlarged sectional view of how a content medium is sprayed from the syringe-type ejecting container illustrated in FIG. 1.

That is to say, by the user pushing the operation shaft 52 of the operation unit 50, as indicated by another arrow outline with a blank inside in FIG. 3, the content medium M applied with spinning force around the container axis line O is pushed to the ejection hole 1a provided in the nozzle 13. Thus, the content medium M is ejected from the ejection hole 1a in the form of atomized particles (including relatively large particles dispersed).

In this way, the ejecting container 1 according to the present embodiment sends the content medium M filled in the ejecting unit 10 out to the ejection hole 1a while applying spinning force to the content medium M, thereby ejecting the content medium M in the form of atomized particles.

Furthermore, the ejecting container 1 according to the present embodiment fills the content medium M in the ejecting unit 10, and therefore, the operation unit 50 for ejecting the content medium M may be configured separately. As a result, only the ejecting unit 10 filled with the content medium M may be downsized without the need for downsizing the operation unit 50. Accordingly, the ejecting container 1 according to the present embodiment is especially effective when only a small amount of the content medium M is desired to be sprayed without compromising the operability. As illustrated in FIG. 1, for example, the ejecting unit 10 may also be used as a cartridge by mounting a cap 15 to the nozzle 13. Additionally, in the present embodiment, as illustrated in FIG. 1, the neck ring 11c is also used as a method of detachably locking the cap 15 to the pipe member 11.

In the ejecting unit 10 according to the present embodiment, the rear end side of the pipe member 11 is sealed by the plunger 12. This allows the content medium M to be filled from above (from the side of the spin element 30), with the front side of the pipe member 11 oriented upward. After the filling of the content medium M, the nozzle 13 embedded with the spin element 30 is attached to form the ejecting unit 10. Accordingly, the ejecting unit 10 according to the present embodiment allows easy filling of the content medium M.

Next, reference is made to FIGS. 5 to 8 that illustrate a syringe-type ejecting container 2 (hereinafter, called "ejecting container 2") according to the second embodiment. In the following, configurations substantially the same as those of the first embodiment are denoted by the same reference numerals, and a description thereof is omitted.

Figure 5A:
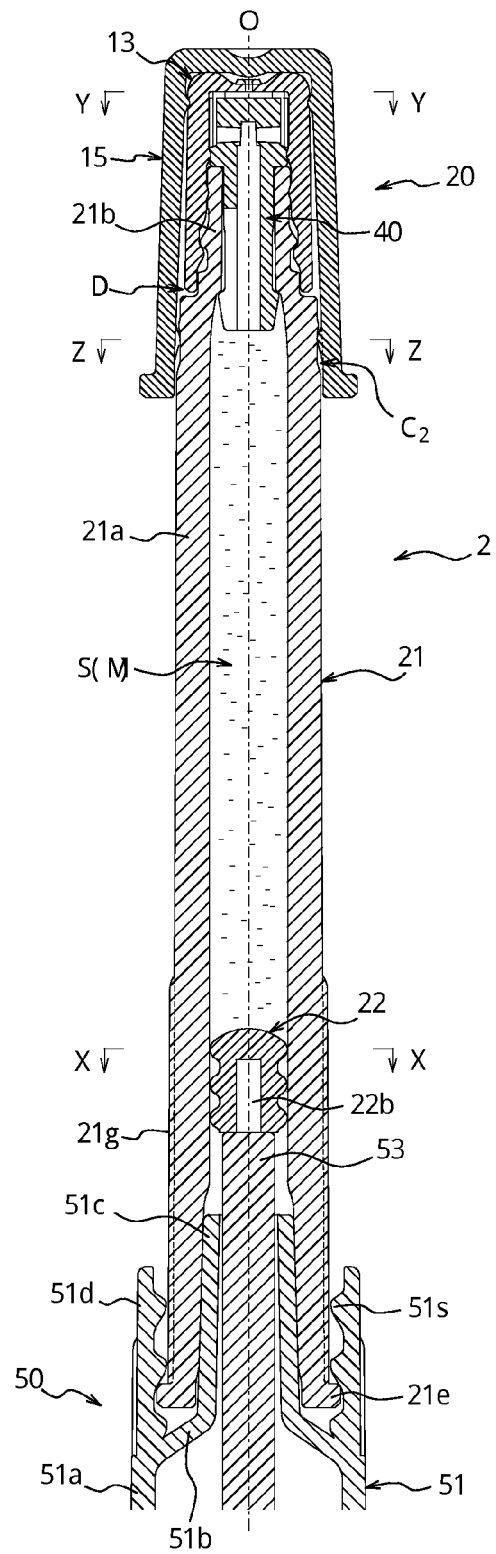
FIG. 5A is an enlarged sectional view of the vicinity of an ejecting unit of a syringe-type ejecting container according to the second embodiment.
Figure 5B:
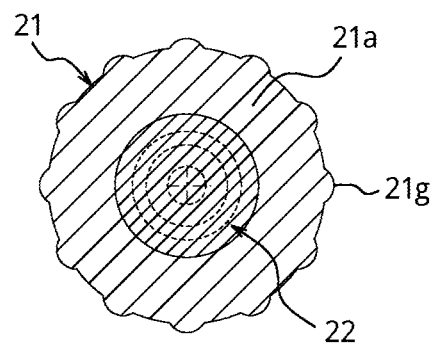
FIG. 5B is a sectional view taken along a line X-X in FIG. 5A.

In FIG. 5, the ejecting container 2 includes the operation unit 50 and an ejecting unit 20. The ejecting unit 20 includes a pipe member 21 that is mounted to the front end tubular portion 51c of the syringe 51. The pipe member 21 includes a main body portion 21a, and within the main body portion 21a, the front end tubular portion 51c of the syringe 51 is accommodated. The pipe member 21 also has a rear end portion 21e that, similarly to the first embodiment, forms a flange portion that serves as a screw portion, and the flange portion is detachably screwed to the inner side of the fitting tubular portion 51d of the syringe 51. This allows the ejecting unit 20 to be screwed to the syringe 51 as in the first embodiment, and accordingly, mounted to the operation unit 50.

The pipe member 21 also includes, in front of the main body portion 21a thereof, a front end portion 21b to which the nozzle 13 is mounted. The front end portion 21b has an outer diameter that is smaller than an outer diameter of the main body portion 21a. That is to say, the front end portion 21b of the pipe member 21 forms an annular step difference D, which extends circumferentially around the container axis line O, with respect to the main body portion 21a. The annular step difference D is configured in a manner such that an outer diameter of the nozzle 13 is equal to or smaller than the outer diameter of the main body portion 21a of the pipe member 21 when the nozzle 13 is mounted to the front end portion 21b of the pipe member 21. This configuration prevents the nozzle 13 from falling off from the pipe member 21 by the rear end of the nozzle 13, which projects relative to an outer circumferential surface of the pipe member 21, being caught by an operator's hand or the like.

Accordingly, the pipe member 21 according to the present embodiment may omit the neck ring 11c provided in the pipe member 11 according to the first embodiment.

In the present embodiment, the main body portion 21a of the pipe member 21 is provided with a plurality of longitudinal ribs 21g that is located at an interval around the container axis line O and that extends along the container axis line O. The longitudinal ribs 21g serve as anti-slippery ribs during operations of the pipe member 21. According to the present embodiment, as a method of connecting the pipe member 21 with the syringe 51, similarly to the first embodiment, an existing method such as undercut fitting taking advantage of irregularities may be selected.

Figure 6:
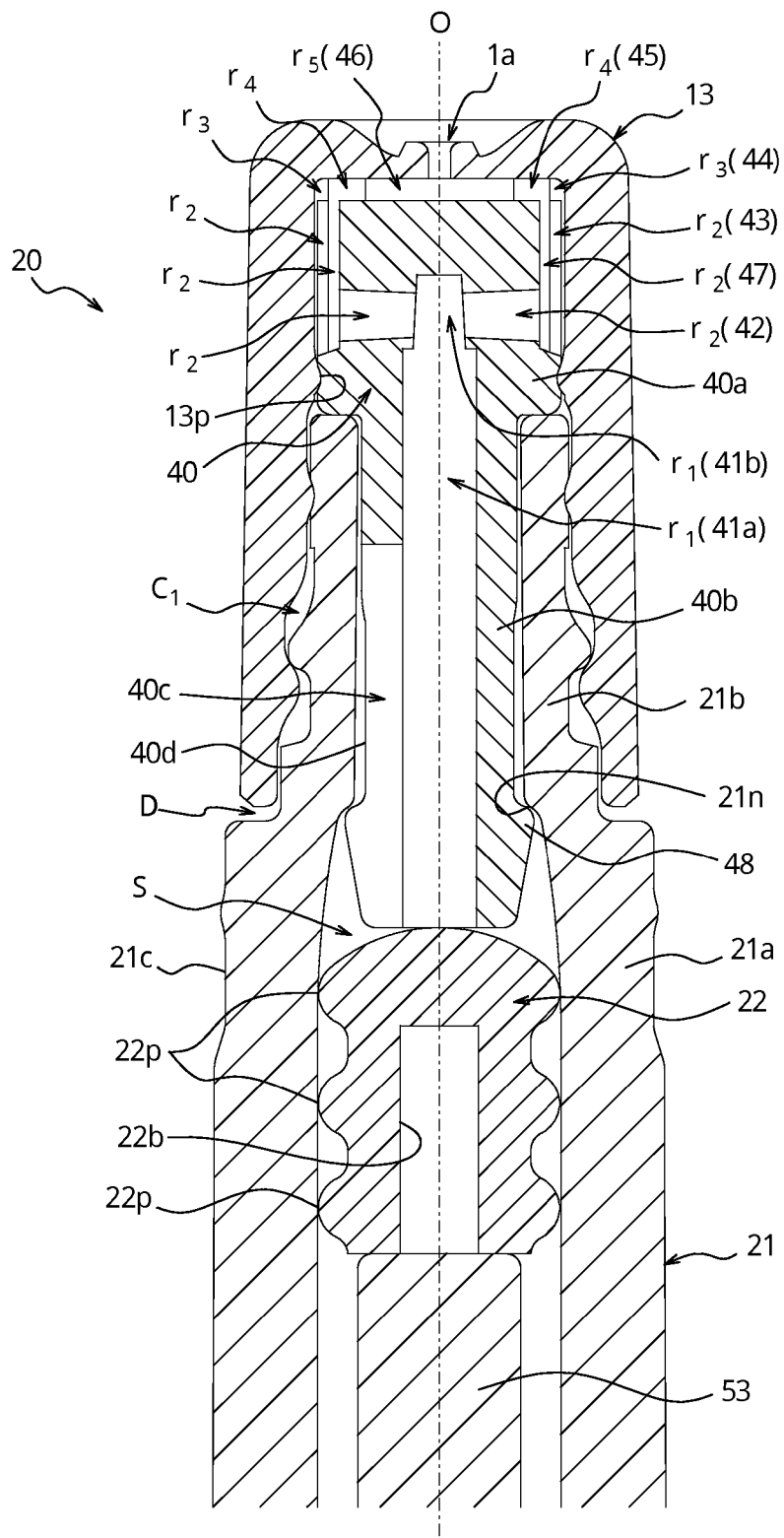
FIG. 6 is an enlarged sectional view of the vicinity of a front end of the ejecting unit illustrated in FIG. 5A.

Furthermore, in the present embodiment, as illustrated in FIG. 6, the plunger 22 has an outer surface that is provided with a plurality of annular grooves extending circumferentially around the container axis line O. That is to say, the outer surface of the plunger 22 is provided with a plurality of annular portions 22p that is located at an interval along the direction of the container axis line O. With the above structure, the present embodiment reduces resistance generated by the sliding contact of the plunger 22 within the pipe member 21 because the annular portions 22p provided in the plunger 22 are merely in local contact with the inner circumferential surface of the pipe member 21. Additionally, as illustrated in FIG. 6, the plunger 22 according to the present embodiment is also formed with a concave portion 22b that opens to a rear end surface of the plunger 22.

Figure 7:
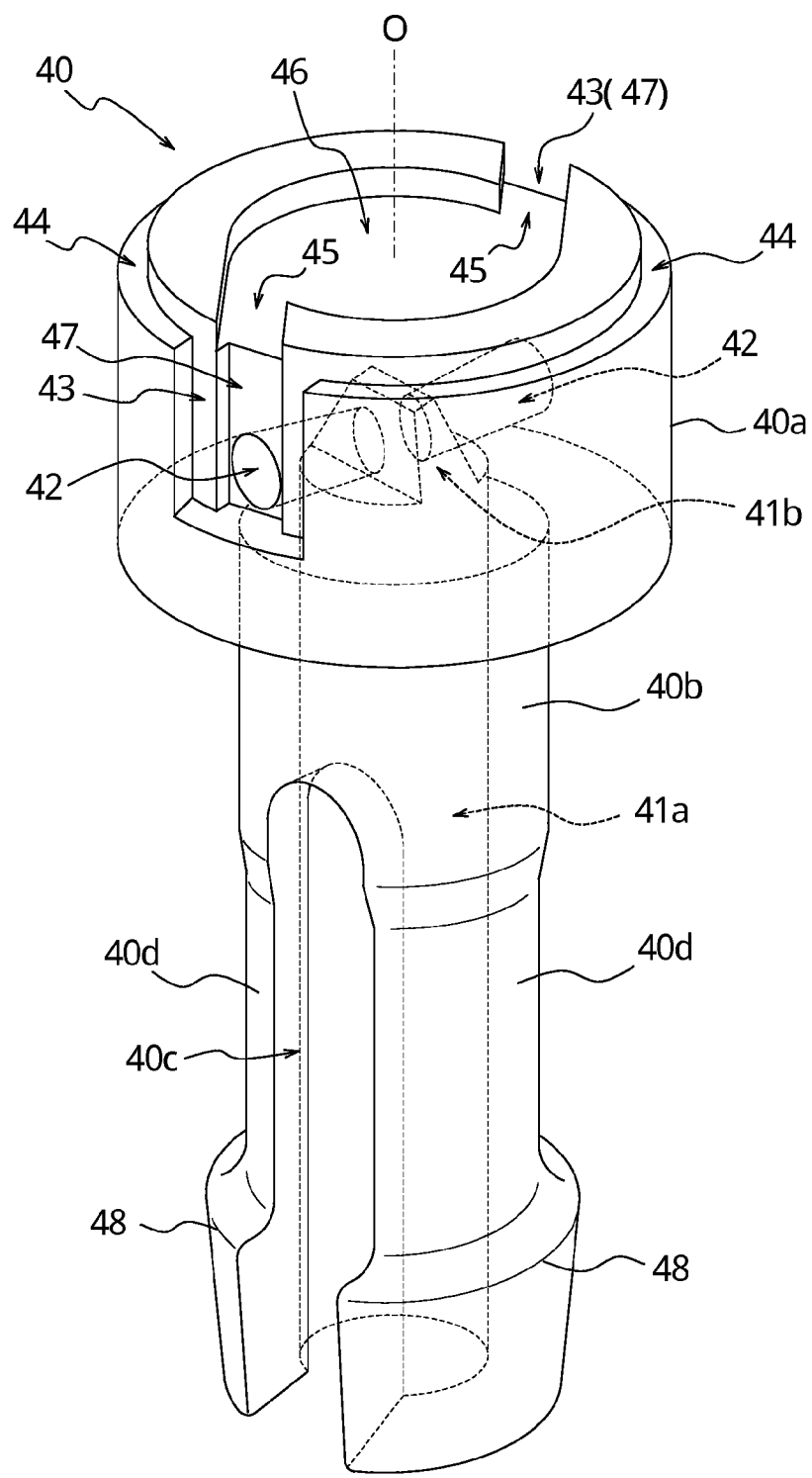
FIG. 7 is a schematic perspective view of a spin element according to FIG. 5A.

Furthermore, in the present embodiment, as illustrated in FIGS. 6 and 7, the spin element 40 includes a main body portion 40a that is arranged between the nozzle 13 and the pipe member 21 and an insertion portion 40b that extends from a rear end of the main body portion 40a and that is inserted into the pipe member 21. By inserting the insertion portion 40b into the pipe member 21, the spin element 40 may be attached to the pipe member 21. That is to say, the ejecting unit 20 may be assembled by the insertion of the insertion portion 40b of the spin element 40 into the pipe member 21 and subsequently by the mounting of the nozzle 13 to the front end portion 21b of the pipe member 21. Accordingly, the assembly of the ejecting unit 20 may be easily completed by a simple operation of attaching the spin element 40 and the nozzle 13 to the pipe member 21 in the stated order.

The nozzle 13 is fixed to the front end portion 21b of the pipe member 21 by a fixing portion $C_1$. Examples of the fixing portion $C_1$ include an undercut fitting portion taking advantage of irregularities as illustrated in the figure. However, the fixing portion $C_1$ is not limited to the undercut fitting portion taking advantage of irregularities and may use any other fixing method such as a screw portion as in the first embodiment.

Furthermore, the insertion portion 40b of the spin element 40 includes a locking portion 48 that is hooked and locked to an inner side of the pipe member 21. In the present embodiment, the locking portion 48 is configured by a projection formed near a rear end of the spin element 40 (the insertion portion 40b). Furthermore, in the present embodiment, as illustrated in FIG. 7, the locking portion 48 is configured by an annular projection extending circumferentially around the container axis line O. As illustrated in FIG. 6, the locking portion 48 is hooked and locked to a stepped portion 21n formed on the inner circumferential surface of the pipe member 21. This configuration firmly holds the spin element 40 to the pipe member 21 by preventing the spin element 40 from slipping off.

Meanwhile, when air accumulates in the filling space S, it is sometimes difficult to expel the accumulated air simply by pushing the plunger 22. In the present embodiment, the insertion portion 40b of the spin element 40 is formed with a cut-out portion 40c. The cut-out portion 40c extends forward from the rear end of the spin element 40. The cut-out portion 40c is formed in at least one location about the container axis line O. The cut-out portion 40c serves to expel the air, together with the content medium M, accumulated in the filling space S, in response to pushing of the plunger 22. Additionally, the spin element 40 according to the present embodiment also includes, on a portion of an outer circumferential surface of the insertion portion 40b, an annular recessed portion 40d extending circumferentially around the container axis line O.

Figure 8A:
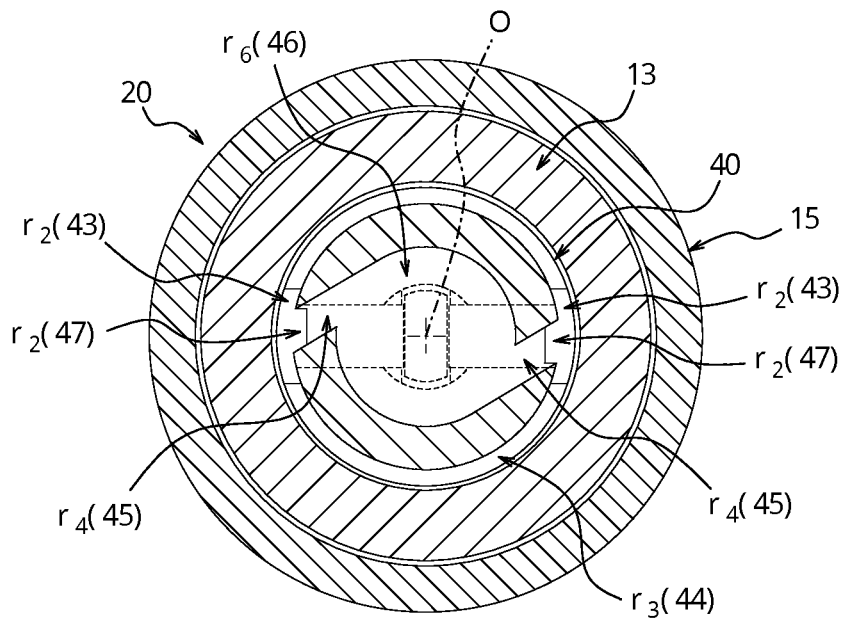
FIG. 8A is a sectional view taken along a line Y-Y in FIG. 5A.

Furthermore, in the present embodiment, the spin element 40 is formed with inner passages (41a and 41b). The inner passages (41a and 41b) open to a rear end surface of the spin element 40. In the present embodiment, as illustrated in FIG. 7, the inner passages (41a and 41b) include a large-diameter passage 41a, which communicates to an opening formed on the rear end surface of the spin element 40, and a flat small-diameter passage 41b, which is tapered forward from the large-diameter passage 41a. The spin element 40 is also formed with at least one (two in the present embodiment) through holes 42 extending from the small-diameter passage 41b in the radial direction. As illustrated in FIG. 7, the spin element 40 also has a lateral surface formed with grooves 43 in correspondence with the positions of the through holes 42. The grooves 43 each extend along the container axis line O and cut out a portion of the front end surface of the spin element 40. The front end surface of the spin element 40 also has a periphery that is formed with an annular cut-out 44 extending circumferentially around the container axis line O. On the front end surface of the spin element 40, swirling grooves 45 connecting to the grooves 43 via the cut-out 44 are formed. As illustrated in FIG. 8A, these two swirling grooves 45 each extend from the cut-out 44 toward the container axis line O while swirling around the container axis line O. Thus, the two swirling grooves 45 join in a cylindrical joining groove 46 formed on the front end surface of the spin element 40.

That is to say, in the present embodiment, by incorporating the insertion portion 40b of the spin element 40 into the pipe member 21 and subsequently by mounting the nozzle 13 to the pipe member 21, as illustrated in FIG. 6, the introduction flow paths $r_1$ (41a and 41b) that communicate with the filling space S of the content medium M, the branched flow paths $r_2$ (42 and 43) that separate the introduction flow paths $r_1$ into two flow paths, the annular flow path $r_3$ (44) that connects the two branched flow paths $r_2$ in an annular form, the two swirling flow paths $r_4$ (45) that connect to the two branched flow paths $r_2$ via the annular flow path $r_3$ (44), and the joining portion $r_5$ (46) that connects the swirling flow paths $r_4$ to the ejection hole 1a are formed between the pipe member 21 and the nozzle 13. In the present embodiment, preferably the grooves 43 are further cut out to form second grooves 47. This helps secure a large flow path area of the branched flow paths $r_2$ formed on the lateral surface of the spin element 40.

Furthermore, as illustrated in FIG. 7, in the present embodiment also, similarly to the first embodiment, each of the branched flow paths $r_2$ (42, 43, and 47) is aligned with the corresponding one of the swirling flow paths $r_4$ (45) via the annular flow path $r_3$ (44). However, in the present embodiment also, similarly to the first embodiment, the branched flow path $r_2$ and the swirling flow path $r_4$ may be arranged to be offset from each other around the container axis line O, so that the annular flow path $r_3$ (44) serves as a bypass flow path. Furthermore, as described earlier, the number of the branched flow paths $r_2$ does not need to correspond to that of the swirling flow paths $r_4$ and may be at least one.

In the present embodiment, as illustrated in FIG. 6, the inner circumferential surface of the nozzle 13 is formed with an annular projection 13p extending circumferentially around the container axis line O. Due to the annular projection 13p, a contacting portion between the inner circumferential surface of the nozzle 13 and an outer circumferential surface of the main body portion 40a of the spin element 40 remains in a liquid-tight state, and positioning of the center (i.e. centering) of the nozzle 13 is accomplished.

Furthermore, the spin element 40 has one end surface (a front end surface) that may be abutted against the inner surface of the front end of the nozzle 13. Accordingly, a contacting portion between the front end surface of the spin element 40 and the inner surface of the front end of the nozzle 13 remains in a liquid-tight state. On the other hand, a rear end surface of the main body portion 40a of the spin element 40 contacts a front end surface (i.e. an end surface of the front end portion 21d) of the pipe member 21. Accordingly, a contacting portion between the rear end surface of the spin element 40 and the front end surface of the pipe member 21 remains in a liquid-tight state. Similarly to the first embodiment, the method of sealing between the rear end surface of the main body portion 40a of the spin element 40 and the front end surface of the pipe member 21 may include a variety of methods.

Basic method of use of the present embodiment is substantially the same as that in the first embodiment. In detail, by the user pushing the operation shaft 52 of the operation unit 50 to send the content medium M out to the ejection hole la while applying spinning force to the content medium M filled in the ejecting unit 20, the content medium M is ejected in the form of atomized particles. In addition, FIG. 6 illustrates a state in which the content liquid M has been ejected.

Figure 8B:
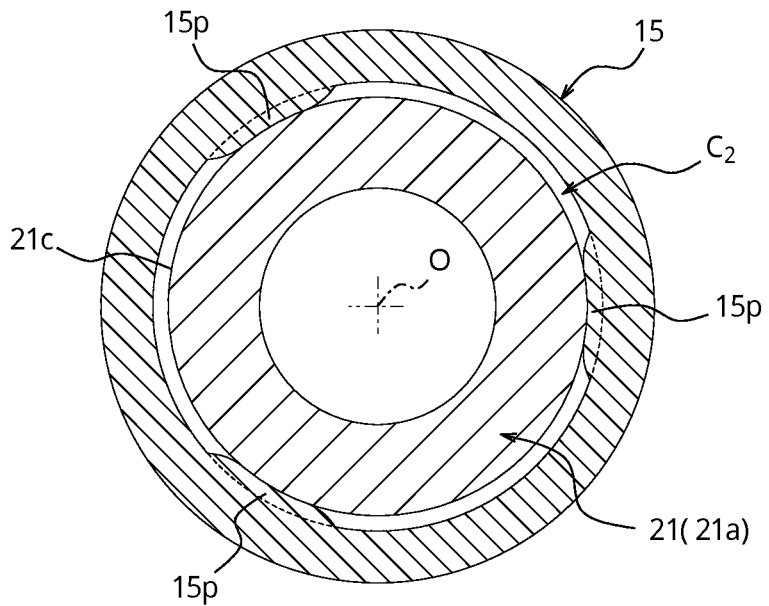
FIG. 8B is a sectional view taken along a line Z-Z in FIG. 5A.

In the present embodiment, as illustrated in FIG. 5A, the cap 15 is detachably mounted to the pipe member 21 by a locking portion $C_2$. As the locking portion $C_2$, as illustrated in FIG. 8B, for example, an inner circumferential surface of the cap 15 may be formed with a plurality of projections 15p located at an interval around the container axis line O, and the main body portion 21a of the pipe member 21 may be formed with an annular recess 21c extending circumferentially around the container axis line O. The projections 15p formed in the cap 15 are detachably locked in the annular recess 21c formed in the pipe member 21. In this way, the cap 15 is detachably mounted to the pipe member 21.

Embodiments described above are considered to be merely optional or exemplary, and various changes may be made within the scope of the claims. For example, in one embodiment, the ejecting units 10 and 20 may be configured to be undetachable from the operation unit 50. Furthermore, in one embodiment, a mesh ring may be mounted to eject the content medium M in the form of foam. Moreover, any of the foregoing features such as the structures adopted in the embodiments may be combined with or replaced by one another as appropriate.

INDUSTRIAL APPLICABILITY

The syringe-type ejecting container according to this disclosure is suitably applied to any type of ejecting container that is intended to be used to eject the content medium. Furthermore, the content medium is not limited to a particular type.

REFERENCE SIGNS LIST 1 syringe-type ejecting container
1a ejection hole
10 ejecting unit (first embodiment)
11 pipe member (first embodiment)
12 plunger (first embodiment)
13 nozzle
20 ejecting unit (second embodiment)
21 pipe member (second embodiment)
22 plunger (second embodiment)
30 spin element (first embodiment)
31 inner passage
32 through hole
33 groove
34 cut-out
35 swirling groove
36 joining groove
40 spin element (second embodiment)
40a main body portion
40b insertion portion
40c cut-out portion
41a inner passage
41b inner passage
42 through hole
43 groove
44 cut-out
45 swirling groove
46 joining groove
47 second groove
48 locking portion
50 operation unit
51 syringe
51a trunk portion
51b shoulder portion
51c front end tubular portion
51d fitting tubular portion
52 operation shaft
53 plunger rod (rod)
$r_1$ introduction flow path
$r_2$ branched flow path
$r_3$ annular flow path
$r_4$ swirling flow path
$r_5$ joining portion

The invention claimed is:

1. A syringe-type ejecting container, comprising:
an operation unit operated by a user; and an ejecting unit through which a content medium is ejected, wherein
the operation unit includes a syringe having a front end tubular portion, a rod extending through an inside of the front end tubular portion, and an operation shaft that causes the rod to project from the front end tubular portion, and
the ejecting unit includes a pipe member that is mounted to the front end tubular portion and that is filled with the content medium, a plunger that is arranged inside the pipe member to push out the content medium, a nozzle that is mounted over an outside of a front end of the pipe member and that is provided with an ejection hole, and a spin element that is arranged inside the nozzle close to the ejection hole and that is configured to circulate the content medium through a branched flow path and a swirling groove to the ejection hole, the branched flow path comprising through holes that branch the path to plural paths, the through holes extending in a radially outer direction.

2. The syringe-type ejecting container of claim 1, wherein the spin element includes a main body portion that is arranged between the nozzle and the pipe member and an insertion portion that is inserted into the pipe member.

3. The syringe-type ejecting container of claim 2, wherein the insertion portion includes a locking portion that is locked to an inner side of the pipe member.

4. The syringe-type ejecting container of claim 2, wherein the insertion portion includes at least one cut-out portion.

5. The syringe-type ejecting container of claim 1, wherein the ejecting unit is detachably mounted to the operation unit.

6. The syringe-type ejecting container of claim 3, wherein the insertion portion includes at least one cut-out portion.

7. The syringe-type ejecting container of claim 2, wherein the ejecting unit is detachably mounted to the operation unit.

8. The syringe-type ejecting container of claim 3, wherein the ejecting unit is detachably mounted to the operation unit.

9. The syringe-type ejecting container of claim 4, wherein the ejecting unit is detachably mounted to the operation unit.

10. The syringe-type ejecting container of claim 6, wherein the ejecting unit is detachably mounted to the operation unit.

* * * * *